US009117680B2

(12) United States Patent
Fisk

(10) Patent No.: US 9,117,680 B2
(45) Date of Patent: Aug. 25, 2015

(54) BIOMEDICAL ELECTRODE

(71) Applicant: Pulse Technologies, Inc., Quakertown, PA (US)

(72) Inventor: Andrew E. Fisk, Philadelphia, PA (US)

(73) Assignee: Pulse Technologies Inc., Quakertown, PA (US)

( * ) Notice: Subject to any disclaimer, the term of this patent is extended or adjusted under 35 U.S.C. 154(b) by 24 days.

(21) Appl. No.: 14/136,810

(22) Filed: Dec. 20, 2013

(65) Prior Publication Data

US 2015/0173635 A1 Jun. 25, 2015

(51) Int. Cl.
*H01L 21/04* (2006.01)
*A61B 5/04* (2006.01)
*A61N 1/05* (2006.01)
*B23K 26/00* (2014.01)
*H01L 31/0224* (2006.01)

(52) U.S. Cl.
CPC ............... *H01L 21/042* (2013.01); *A61B 5/04* (2013.01); *A61N 1/05* (2013.01); *B23K 26/0078* (2013.01); *H01L 31/0224* (2013.01)

(58) Field of Classification Search
CPC .................... H01L 21/042; H01L 31/0224
See application file for complete search history.

(56) References Cited

U.S. PATENT DOCUMENTS

| 5,318,572 A | 6/1994 | Helland et al. |
| 5,571,158 A | 11/1996 | Bolz et al. |
| 6,799,076 B2 | 9/2004 | Gelb et al. |
| 2007/0225785 A1 | 9/2007 | Park et al. |
| 2008/0183260 A1* | 7/2008 | Nygren .................. 607/119 |
| 2008/0299289 A1 | 12/2008 | Fisk |
| 2011/0160821 A1 | 6/2011 | Jackson et al. |
| 2014/0357973 A1 | 12/2014 | Fisk |

FOREIGN PATENT DOCUMENTS

| EP | 2808053A1 A1 | 12/2014 |
| WO | W02007095549A2 A2 | 8/2007 |

OTHER PUBLICATIONS

Vorobyev, A.Y., and Chunlei Guo, "Femtosecond Laser Nanostructuring Ofmetals." Optics Press, vol. 14, No. 6; Mar. 20, 2006; pp. 2164-2169.
EP2886155 European Search Report.
EP2886155 European Written Opinion.

* cited by examiner

*Primary Examiner* — Elias M Ullah
(74) *Attorney, Agent, or Firm* — Roberts & Roberts, LLP

(57) ABSTRACT

A biocompatible, implantable electrode for electrically active medical devices. The implantable medical electrode has a surface geometry which optimizes the electrical performance of the electrode, while mitigating the undesirable effects associated with prior art porous surfaces. The electrode has an optimized surface topography for improved electrical performance. Such a electrode is suitable for devices which may be permanently implanted in the human body as stimulation electrodes, such as pacemakers, or as sensors of medical conditions. Such is achieved by the application of ultrafast high energy pulses to the surface of a solid, monolithic electrode material for the purpose of increasing the surface area and thereby decreasing its after-potential polarization.

20 Claims, 10 Drawing Sheets

Trial 1: Polarization = 456mV

100 "pulses" per "spot"

(a)
Macro image of part (b)
Hillock structure (c)
Hillock structure <10micron (d)
Periodic structure on hillock is barely visible (e)
Nanoglobules have high sphericity Trial 2: Polarization = 105mV 300 "pulses" per "spot"

(a)
Macro image of part (b)
Hillock structure (c)
Hillock structure >10micron (d)
Periodic structure on hillock is visible (e)
Nanoglobules have sphericity with some tubular features Trial 3: Polarization = 45mV 500 "pulses" per "spot"

(a)
Macro image of part (b)
Hillock structure (c)
Hillock structure ~25micron (d)
Periodic structure on hillock is pronounced (e)
Nanoglobules are angular with large voids and cavities Trial A: Polarization = 410mV Spot Size: 50 micron Step Offset: 35 micron (a)
Macro image of part (b)
Hillock structure (c)
Hillock structure ~8 micron,
Spacing of hillock corresponds to offset step (d)
Periodic structure on hillock (e)
Nanoglobules are angular with low sphericity Trial B: Polarization = 365mV Spot Size: 50 micron Step Offset: 35 x 25 micron (a)
Macro image of part (b)
Hillock structure (c)
Hillock structure ~25 micron (d)
Periodic structure on hillock walls (e)
Nanoglobules are angular with low sphericity with large voids Trial C: Polarization = 490mV Spot Size: 50micron Step Offset: 35 x 50 micron (a)
Macro image of part (b)
Hillock structure forms ridges due to offest (c)
Hillock structure is very shallow (d)
Periodic structure on hillock walls (e)
Nanoglobules have sphericity with few voids Trial D: Polarization = 710mV Spot Size: 50micron Step Offset: 50 x 50 micron (a)
Macro image of part (b)
Hillock structure forms ridges due to offest (c)
Hillock structure is very shallow (d)
Periodic structure on hillock walls (e)
Nanoglobules having a mixture a tubular structure Trial E: Polarization = 185mV Spot Size: 50micron Step Offset: 25 x 25 micron (a)
Macro image of part (b)
Hillock structure forms ridges due to offest (c)
Structure showing deep Hillock features, some period structures can be seen on the hillock walls (d)
Nanoglobules having sphericity and deep voids Trial F: Polarization = 525mV Spot Size: 100micron Step Offset: 70 x 70 micron (a)
Macro image of part (b)
Hillock structure offest Hillock features proportional to offset (c)

Period structure can be seen on the hillock walls
(d)

(e)
Nanoglobules having sphericity and few voids

Trial G: Polarization = 630mV

Spot Size: 200micron

Step Offset: 140 x140 micron (a)
Macro image of part (b)
Hillock structure offest Hillock features proportional to offset (c)

Period structure can be seen on the hillock walls
(d)

(e)
Nanoglobules having tubular structures and few voids

BIOMEDICAL ELECTRODE

BACKGROUND OF THE INVENTION

1. Field of the Invention

The present invention relates to a biomedical, implantable electrode for electrically active medical devices. The electrode has an improved surface topography for enhanced electrical performance. Such an electrode is suitable for devices which may be permanently implanted in the human body as stimulation electrodes, for example, as pacemakers, or sensors of medical conditions. This is achieved by the application of ultrafast, high energy pulses to the surface of a solid, monolithic electrode material for the purpose of increasing the surface area and thereby decreasing its after-potential polarization.

2. Description of the Related Art

There is great commercial interest in producing active implantable devices which are typically electrodes used for the stimulation of tissue or the sensing of electrical biorhythms. The electrical performance of implantable electrodes can be enhanced by increasing the external surface area which is in contact with tissues inside the body. It is known that increasing the surface area of an implantable electrode increases the double layer capacitance of the electrode and reduces the after-potential polarization, thereby increasing device battery life, or allowing for lower capture thresholds, and improved sensing of certain electrical signals, such as R and P waves. It is known in the art to apply a coating to increase the surface area of the electrode thereby reducing the after-potential polarization. A reduction in after-potential polarization results in an increase in charge transfer efficiency by allowing increased charge transfer at lower voltages. This is of particular interest in neurological stimulation. Double layer capacitance is typically measured by means of electrochemical impedance spectroscopy. In this method an electrode is submerged in a electrolytic bath and a small cyclic wave is imposed on the electrode. The current and voltage response of the electrode/electrolyte system is measured to determine the double layer capacitance. The capacitance is the predominant factor in the impedance at low frequencies (<10 Hz) and thus the capacitance is typically measured at frequencies of 0.001 Hz-1 Hz.

The current state of the art for increasing the surface area of an implantable electrode is to apply a suitable coating to the surface of electrode substrates. A principal concern in any coating application is the joining of the substrate and coating material and the adhesion between them. In this regard, U.S. Pat. No. 5,571,158 shows a stimulation electrode having a porous surface coating whose active surface area is essentially larger than the surface area defined by the geometrical basic shape of the electrode. U.S. Pat. No. 6,799,076 discloses an electrode having a substrate with a first layer covering at least a portion of the substrate, and a second layer covering at least a portion of the first layer. The first layer consists of a carbide, nitride or carbonitride of titanium, vanadium, zirconium, niobium, molybdenum, hafnium, tantalum or tungsten. The second layer includes iridium. U.S. Pat. No. 5,318,572 teaches a high efficiency tissue stimulating and signal sensing electrode. A lead has a porous electrode of platinum-iridium with recessed areas or grooves formed into the surface. The grooves allow for acute electrode stabilization as a result of clot formation and endocardial tissue capture. At least one layer of a porous coating of 20-200 micron diameter spherical particles are deposited on the surface of the base electrode to obtain a porous macrostructure for promoting chronic tissue ingrowth. A microstructure surface coating is applied to increase the active surface area and enhance electrical efficiency by lowering electrochemical polarization and increasing electrical capacitance.

A particular concern for these techniques is that a section of coating might become dislodged in use and become an irritant. Current techniques for testing the adhesion of a coating to a substrate results in the destruction of the test piece which is costly and requires statistical evidence to validate the test method and sampling. A better alternative to a coating would be the modification of the electrode substrate material itself, thereby eliminating the issue of poor adhesion and the potential of coating particles becoming dislodged during use. Prior attempts to produce a suitable modified surface which does not include a coating have failed due to mechanical limitations. An example is found in U.S. patent publication 2011/0160821 where the surface is laser etched, thus producing ridges with features 25,000 nm to 250,000 nm. For a suitable electrode, the surface features need to be sub-millimeter, for example, from about 1 nm to about 1000 nm. Others have taught laser ablation of electrode surfaces, however, such techniques cannot achieve the nanometer scale feature size of this invention.

The present invention solves these issues by the application of ultra-fast energy pulses supplied to the surface. It has now been found that energy pulses delivered by means of an ultrafast laser produces surface structures on the order of 50 nm to 500 nm which is ideal for tissue stimulation. This process is produced not by laser etching and removal of material but by a restructuring of the surface. In the laser etching process of U.S. patent publication 2011/0160821 the surface is modified through the impingement of the laser, and the smallest feature that can be made equates to the size of the focused laser beam, which is limited by the wavelength of the laser, typically 200-1600 nm.

It has now been found that an important factor in obtaining the desired surface topography for enhanced electrical performance is in the form of a three tiered surface structure. The three structural tiers are described in terms of nano, micro and macro structures. The nano-structures are described as nanoglobules which are manifested as rounded tubes or spherical globules which are almost powdery in appearance but well adhered to the surface. The sphericity of the nanoglobules decreases with an increasing number of laser irradiation pulses per spot. These nanoglobules are superimposed on a hillock-like microstructure in a periodic pattern determined by the wavelength of the laser where the lower the wavelength the smaller the period of the pattern. This microstructure pattern is superimposed on somewhat larger macro structure which resemble ranges of mesas. As discussed more fully below, the macro protrusions have a width in the range of from about 0.15 μm to about 50 μm; the micro protrusions have a width ranging from about 0.15 μm to about 5 μm; and the nano protrusions have a width ranging from about 0.01 μm to about 1 μm. In an embodiment of the invention, the surface may also have voids which extend down into the substrate surface in addition to these outwardly extending protrusions or uplifts.

SUMMARY OF THE INVENTION

The invention provides an electrode comprising a solid, monolithic substrate having an outer peripheral surface; the outer peripheral surface having a topography defined by a plurality of discrete macro protrusions distributed about and extending outwardly from the outer peripheral surface, the macro protrusions having a width in the range of from about 0.15 μm to about 50 μm; a plurality of discrete micro protrusions distributed on and extending outwardly from the macro protrusions, the micro protrusions having a width ranging from about 0.15 µm to about 5 µm; and a plurality of discrete nano protrusions distributed on and extending outwardly from the micro protrusions, the nano protrusions having a width ranging from about 0.01 µm to about 1 µm.

The invention also provides a method for producing an electrode comprising a solid, monolithic substrate having an outer peripheral surface; the outer peripheral surface having a topography defined by a plurality of discrete macro protrusions distributed about and extending outwardly from the outer peripheral surface, the macro protrusions having a width in the range of from about 0.15 µm to about 50 µm; a plurality of discrete micro protrusions distributed on and extending outwardly from the macro protrusions, the micro protrusions having a width ranging from about 0.15 µm to about 5 µm; and a plurality of discrete nano protrusions distributed on and extending outwardly from the micro protrusions, the nano protrusions having a width ranging from about 0.01 µm to about 1 µm; the method comprising exposing a solid, monolithic substrate to pulses of laser irradiation having a laser spot diameter ranging from about 1 µm to about 1000 µm, wherein the number of pulses of laser irradiation per spot, ranges from about 10 to about 1500 pulses, the pulse wavelength ranges from about 200 nm to about 1500 nm, the pulse width ranges from about 1 femtosecond to about 5 picoseconds; at a irradiance of from about 200 watts/cm$^2$ to about 5000 watts/cm$^2$.

DESCRIPTION OF THE INVENTION

Figure 1:
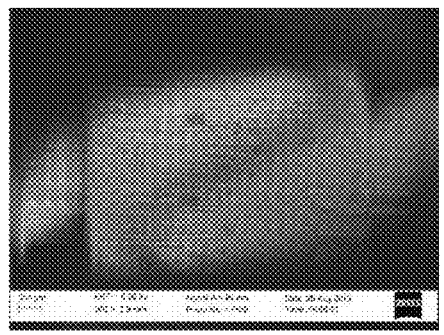
FIG. 1 shows an SEM of the substrate structure obtained according to Example 1, Trial 1.
Figure 1:
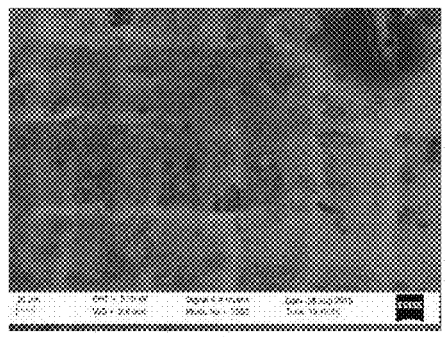
Figure 1:
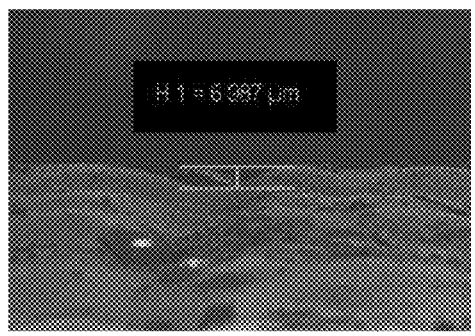
Figure 1:
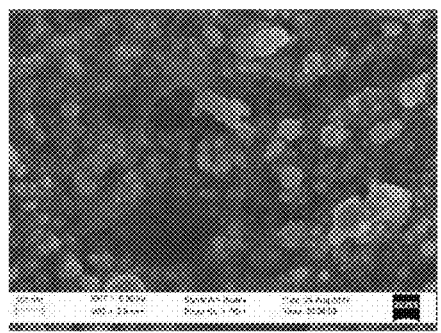
Figure 1:
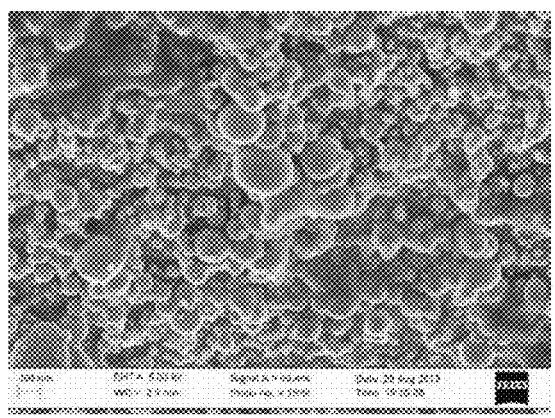

Surface morphologies of implanted biomedical electrodes are designed to improve interaction with surrounding tissues. The invention provides biological benefits such as a reduced likelihood of infection, and functional benefits such as improved electrical transfer. The invention produces features on biocompatible metals such as platinum by exposure to a femtosecond laser operating at various wavelengths. The invention realizes a performance advantage over typical prior art surface modifications by achieving an optimal surface geometry, which maximizes the effective surface area of the electrode while minimizing the after-potential polarization effect, thereby increasing charge transfer efficiency. After-potential polarization is the voltage remaining on an electrode after a stimulation pulse on the electrode from a device such as a pacemaker. It is a measure of how efficiently the charge is injected into the tissue.

It is known that the method for charge transfer in a medical electrode is by the charging and discharging of the electrical double layer capacitance formed on the surface of the electrode. This layer can be thought of as a simple parallel plate model in which the tissue to be stimulated is separated from the electrode surface by a barrier primarily of water, Na, K and Cl. The thickness of this layer is dictated by the concentration of the electrolyte in the body and is therefore uniform over the working life of the electrode. The thickness of an electrical double layer formed by an electrical conductor in 0.9% saline, i.e., body fluid is on the order of 1 nm and the expected thickness of the double layer capacitance formed in normal body electrolyte would be from about 0.5 nm to about 10 nm, more typically from about 5 to about 6 nm.

A typical human cell is on the order of from about 5,000 nm to about 10,000 nm in size. Because the cells are much larger than the layer and much smaller than the electrode surface, the cells can be thought of as being parallel to the surface of the electrode. As the non-polarized electrolyte (the electrolyte present but not participating in the electrical double layer) increases, the impedance of the tissue-electrode system increases. This is known as the solution resistance. The increased impedance results in a less effective charge transfer due to a dissipation of voltage along the solution resistance path. To minimize this impedance, the tissue to be stimulated should be as close to the electrode surface as possible. It would therefore be preferred, for these purposes, to have the electrode surface flat and placed parallel to the tissue.

The invention thus provides an electrode comprising a solid, monolithic substrate having an outer peripheral surface. The substrate comprises a biocompatible metal suitable for implanting within the tissues of a mammal. Examples non-exclusively include platinum, steel, alloys of platinum and iridium, alloys of nickel and cobalt, and combinations thereof. In one embodiment, the outer peripheral surface of an electrode has an area of from about 1 mm$^2$ to about 20 mm$^2$, preferably from about 3 mm$^2$ to about 12 mm$^2$. The electrode may have any suitable configuration or shape such as a tubular, flat, mushroom or corkscrew shape.

The outer peripheral surface has a topography defined by a plurality of discrete macro protrusions distributed about and extending outwardly from the outer peripheral surface. In one embodiment, the macro protrusions are substantially uniformly distributed across the outer peripheral surface of the solid, monolithic substrate. In one embodiment, the macro protrusions have a width in the range of from about 0.15 µm to about 50 µm. In another embodiment, the macro protrusions have a width in the range of from about 0.2 µm to about 30 µm. In yet another embodiment, the macro protrusions have a width in the range of from about 1 µm to about 20 µm.

A plurality of discrete micro protrusions are distributed on and extend outwardly from the macro protrusions. In one embodiment, the micro protrusions have a width ranging from about 0.15 µm to about 5 µm. In another embodiment, the micro protrusions have a width in the range of from about 0.2 µm to about 2 µm. In yet another embodiment, the micro protrusions have a width in the range of from about 0.4 µm to about 1.5 µm. In one embodiment the micro protrusions are distributed across the macro protrusions in the form of periodic waves of the heights of the micro protrusions. It is believed that the periodic waves are caused and controlled by the wavelength of the laser irradiation.

A plurality of discrete nano protrusions are distributed on and extending outwardly from the micro protrusions. In one embodiment, the nano protrusions have a width ranging from about 0.01 μm to about 1 μm. In another embodiment, the nano protrusions have a width in the range of from about 0.02 μm to about 1 μm. In yet another embodiment the nano protrusions have a width in the range of from about 0.075 μm to about 0.8 μm. 4. In one embodiment, the nano protrusions are distributed across the micro protrusions in the form of tubes and/or globules. It is believed that the nano protrusions are caused and controlled by the number of pulses and the pulse duration. Without being held to a particular theory, it is believed that the macro, micro and nano protrusions are formed by the laser drilling voids in the substrate surface, and then the materials from the voids are re-deposited onto the substrate surface as these protrusions. It is therefore important that the laser irradiation is done without purging the substrate with a gas and without any substantial gas pressure since such would tend to blow the void material away rather than re-depositing it onto the substrate. It is believed that the atmosphere in which laser irradiation is conducted is not important as long as the removed void material is not blown away, and is allowed to re-deposit onto the substrate. This drilling effect is most intense at the center of the laser spot, and therefore the traversing of the laser spot across the substrate surface causes an overlapping of spots, and therefore a Gaussian distribution of applied laser radiation.

In another embodiment of the invention, in addition to these discrete macro, micro, and nano protrusions which extend outwardly from the substrate surface, the surface structure may have a laser induced array of voids whose length and depth depend on the laser parameters employed. Thus in this embodiment, the outer peripheral surface additionally has a topography with a plurality of voids distributed about the outer peripheral surface which extending a depth through the substrate. The voids have a depth through the substrate of from about 50 nm to about 500 nm, preferably from about 100 nm to about 250 nm. The voids have a width of from about 50 nm to about 500 nm, preferably of from about 100 nm to about 250 nm. The voids are spaced from adjacent voids a distance of from about 50 nm to about 250 nm.

An electrode according to the invention, is produced by exposing an outer peripheral surface of a solid, monolithic substrate of a biocompatible metal to pulses of laser irradiation. In one embodiment the laser has a spot diameter ranging from about 1 μm to about 1000 μm. In another embodiment, the laser has a spot diameter ranging from about 2 μm to about 250 μm, and in yet another embodiment, the laser has a spot diameter ranging from about 5 μm to about 200 μm. In one embodiment the number of pulses of laser irradiation per spot, ranges from about 10 to about 1500 pulses. In another embodiment, the number of pulses of laser irradiation per spot ranges from about 20 to about 1000, and in yet another embodiment, the number of pulses of laser irradiation per spot ranges from about 100 to about 500. In one embodiment the laser has a pulse wavelength which ranges from about 200 nm to about 1500 nm. In another embodiment, the pulse wavelength ranges from about 400 to about 1,000, and in yet another embodiment, the pulse wavelength ranges from about 400 to about 800. In one embodiment the laser pulse width ranges from about 1 femtosecond to about 5 picoseconds. In another embodiment the laser pulse width ranges from about 1 femtoseconds to about 3 picoseconds. In one embodiment the laser irradiance ranges from about 200 watts/cm$^2$ to about 5000 watts/cm$^2$. The exposing may be conducted by traversing the spot of laser radiation across the outer peripheral surface of the solid, monolithic substrate at a rate of from about 50 mm/min to about 1000 mm/min, however, the rate is not critical to the invention and only affects the cost effective execution of the inventive method.

Examples of suitable lasers non-exclusively include a Coherent Libra-F Ti:Sapphire amplifier laser system, a Rofin Startfemto, and a Coherent AVIA laser. According to the invention, the resulting electrode has a polarization of about 1,000 mV or less, preferably about 500 mV or less, and more preferably about 200 mV or less. It has been determined that the lower the polarization of the electrode, the more optimized is the surface topography for improved electrical performance. The desirable characteristics of the surface, those being high double layer capacitance of the electrode and a low after-potential polarization effect, are enhanced when the surface area of the electrode is increased. A reduction in after-potential polarization results in an increase in charge transfer efficiency by allowing increased charge transfer at lower voltages. Thus a reduction of after-potential polarization increases device battery life, and improves sensing of certain electrical signals.

In use, the inventive electrode has at least one electrical connector electrically attached at an end thereof to the substrate. Typically, this may be a wire of a suitable material such as a biocompatible, conductive material such as platinum, silver, copper, a superalloy such as MP35N, or a superplastic such as Nitrol. In one embodiment, the other end of the wire is connected to an electrical pulse generator such as a cardiac pacemaker. In another embodiment, the other end of the wire is connected to an electrical measurement device such as a sensor of biological conditions, or a voltage recording device.

The following non-limiting examples serve to illustrate the invention.

EXAMPLE 1

A series of cylindrical platinum electrodes having a diameter of 2.05 mm and an active length of 2.5 mm were processed via ultrafast laser texturing. Each of the cylinders was rotated on its axis head, translated via mechanical stages and a series of pulses were delivered. The sample was positioned under the laser while the laser impinged the surface at a nearly oblique angle and the number of pulses varied. Variations in operating parameters give the indicated potential polarization results. A Coherent Libra-F Ti:Sapphire amplifier laser system was used for the exposure. The nominal spot size was 105 μm. The offset step between spot centers was 70 μm with a 30% overlap. The desirable after potential polarization is <20 mV. The pulse duration was ~100 pf, the pulse energy was ~1 mJ, and the repetition frequency was 1 kHz.

Trial 1

Comparative

In this example, 100 pulses per spot were delivered. The scanning electron micrograms (SEMs) of FIG. 1 show the resulting structure. Image (a) shows a macro image of the substrate. Images (b)-(c) show the micro hillock structure having a height <10 μm. Image (d) shows a periodic structure on the micro hillock structure which is barely visible. Image (e) shows nanoglobules having high sphericity. The polarization was 456 mV.

Trial 2

Figure 2:
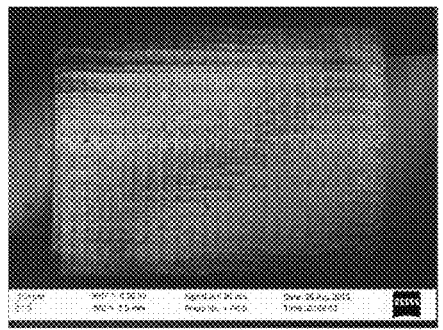
FIG. 2 shows an SEM of the substrate structure obtained according to Example 1, Trial 2.
Figure 2:
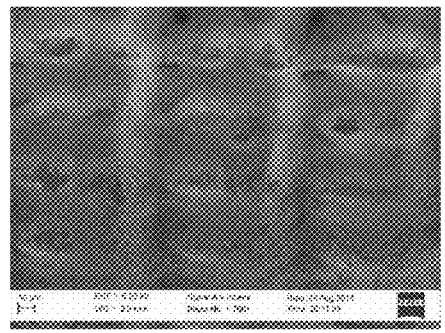
Figure 2:
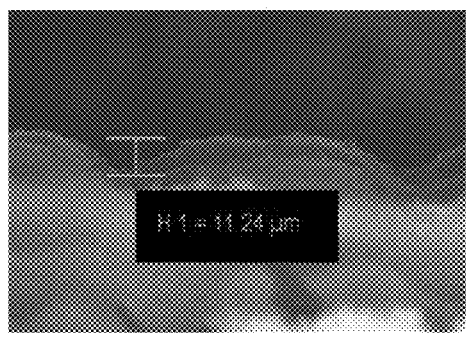
Figure 2:
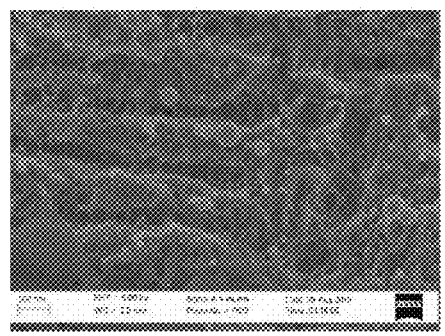
Figure 2:
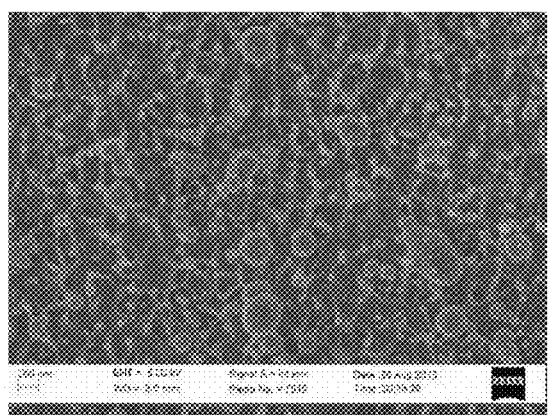

In this example, 300 pulses per spot were delivered. The scanning electron micrograms (SEMs) of FIG. 2 show the resulting structure. Image (a) shows a macro image of the substrate. Images (b)-(c) show the micro hillock structure having a height >10 μm. Image (d) shows a periodic structure on the micro hillock structure which is visible. Image (e) shows nanoglobules having sphericity with some tubular features. The polarization was 105 mV.

Trial 3

Figure 3:
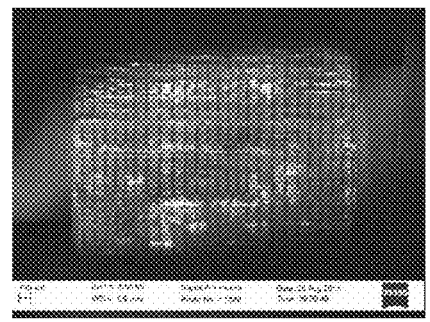
FIG. 3 shows an SEM of the substrate structure obtained according to Example 1, Trial 3.
Figure 3:
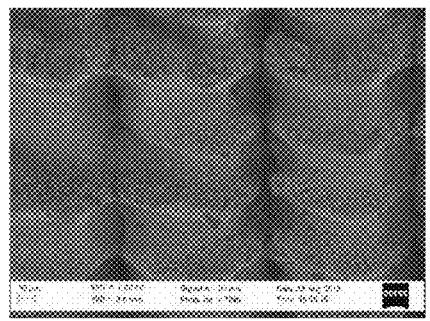
Figure 3:
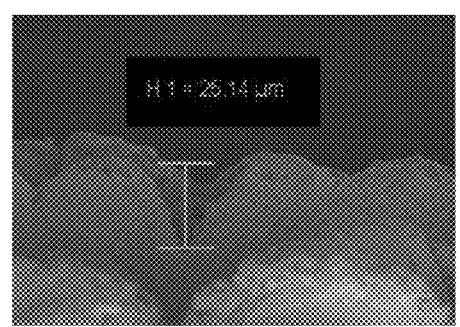
Figure 3:
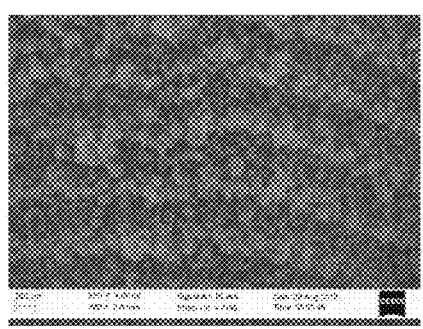
Figure 3:
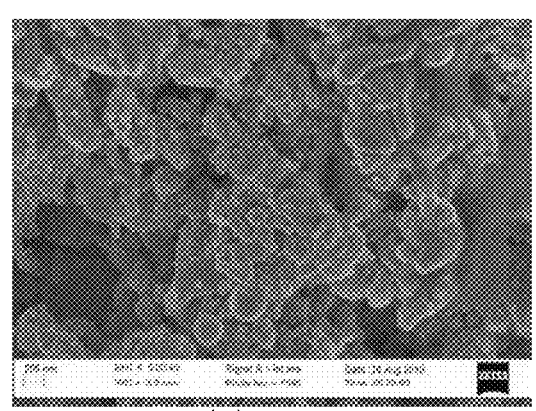

In this example, 500 pulses per spot were delivered. The scanning electron micrograms (SEMs) of FIG. 3 show the resulting structure. Image (a) shows a macro image of the substrate. Images (b)-(c) show the micro hillock structure having a height ~25 μm. Image (d) shows a periodic structure on the micro hillock structure which is pronounced. Image (e) shows angular nanoglobules and large voids and cavities. The polarization was 45 mV.

EXAMPLE 2

A series of cylindrical platinum electrodes having a diameter of 2.05 mm and an active length of 2.5 mm were processed on 30% of their surface via ultrafast laser texturing. Each of the cylinders was rotated on its axis head, translated via mechanical stages and a series of pulses were delivered. The sample was positioned under the laser while the laser impinged the surface at a nearly oblique angle. Variations in operating parameters give the indicated potential polarization results. A Rofin StarFrmto FX laser system was used for the exposure. The nominal spot size was varied at 50 μm, 100 μm and 200 μm. The offset step between spot centers was varied at 25 μm, 35 μm, 50 μm, 70 μm, and 140 μm between spot centers. The number of pulses per spot was 500. The desirable after potential polarization is <5500 mV in this configuration due to the reduced processed surface size as compared to Example 1. In this Example 2, the laser exposure had a fixed wavelength of 800 nm.

Trial A

Figure 4:
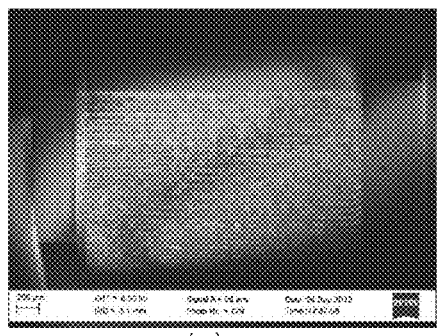
FIG. 4 shows an SEM of the substrate structure obtained according to Example 2, Trial A.
Figure 4:
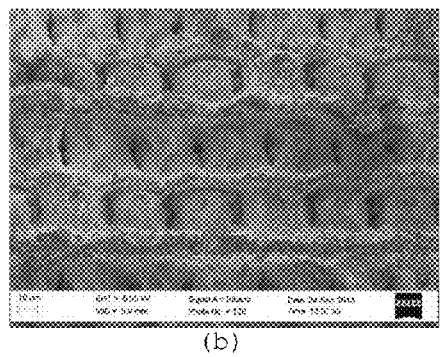
Figure 4:
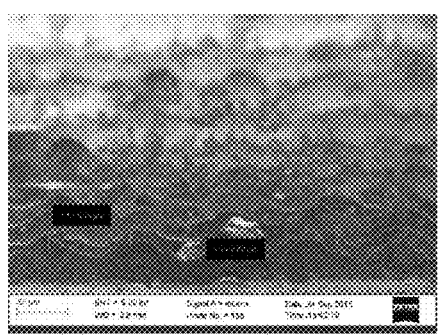
Figure 4:
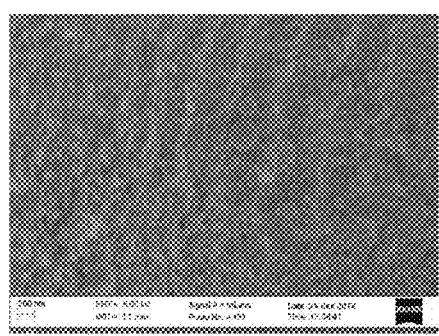
Figure 4:
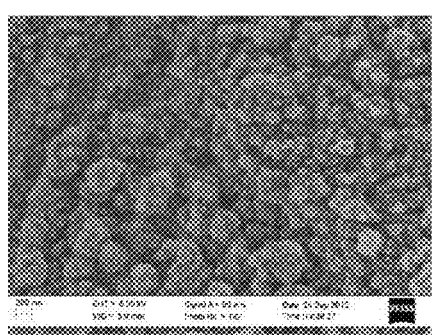

In this example, spot size was 50 μm and the offset step was 35 μm. The scanning electron micrograms (SEMs) of FIG. 4 show the resulting structure. Image (a) shows a macro image of the substrate. Images (b)-(c) show the micro hillock structure of ~8 μm which corresponds to the offset step. Image (d) shows a periodic structure on the micro hillock structure. Image (e) shows angular nanoglobules with low sphericity. The polarization was 410 mV.

Trial B

Figure 5:
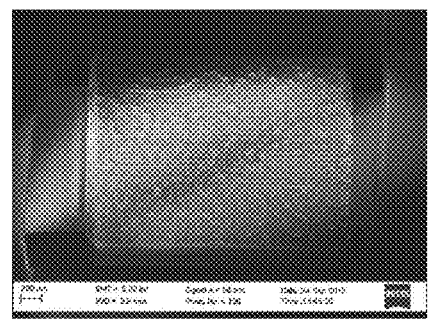
FIG. 5 shows an SEM of the substrate structure obtained according to Example 2, Trial B.
Figure 5:
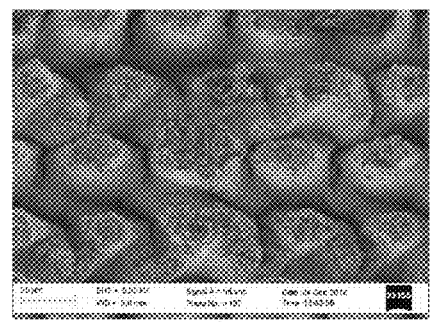
Figure 5:
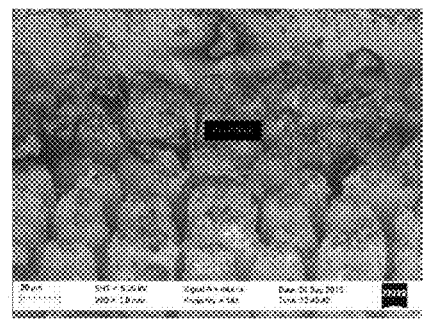
Figure 5:
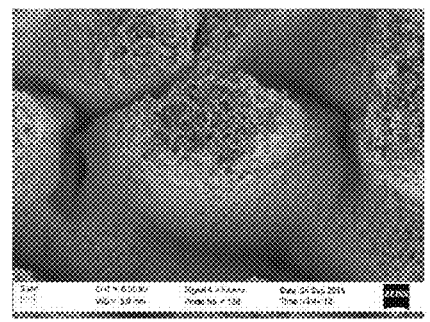
Figure 5:
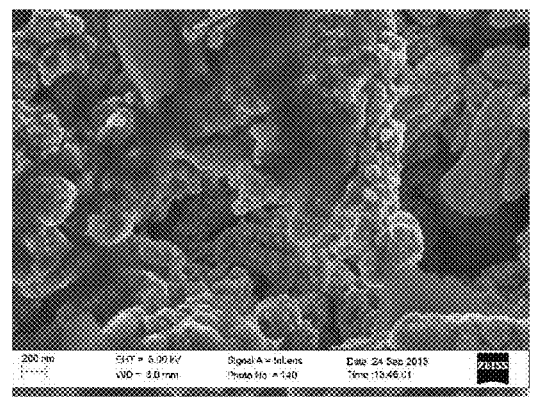

In this example, spot size was 50 μm and the offset step was 35 μm×25 μm. The scanning electron micrograms (SEMs) of FIG. 5 show the resulting structure. Image (a) shows a macro image of the substrate. Images (b)-(c) show the micro hillock structure of ~25 μm. Image (d) shows a periodic structure on the micro hillock walls. Image (e) shows angular nanoglobules with low sphericity and with large voids. The polarization was 365 mV.

Trial C

Figure 6:
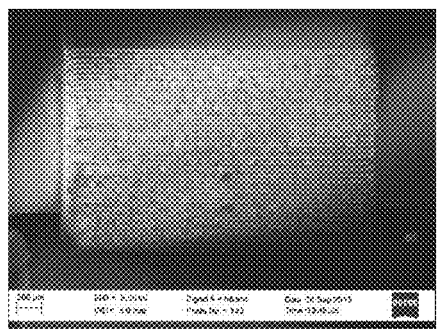
FIG. 6 shows an SEM of the substrate structure obtained according to Example 2, Trial C.
Figure 6:
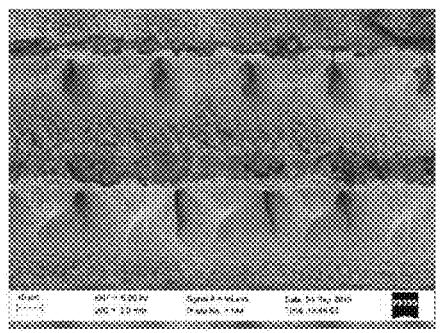
Figure 6:
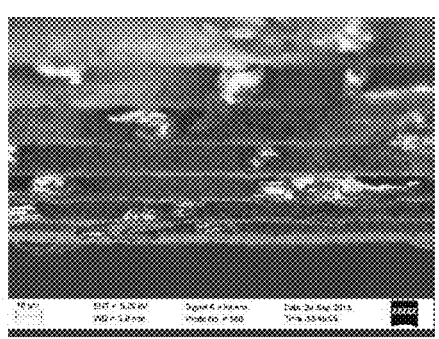
Figure 6:
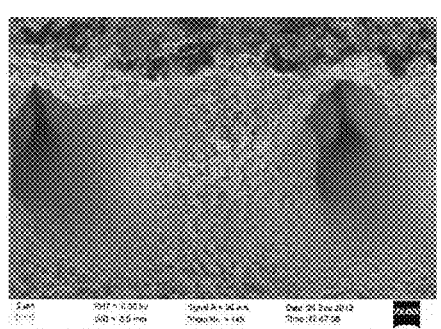
Figure 6:
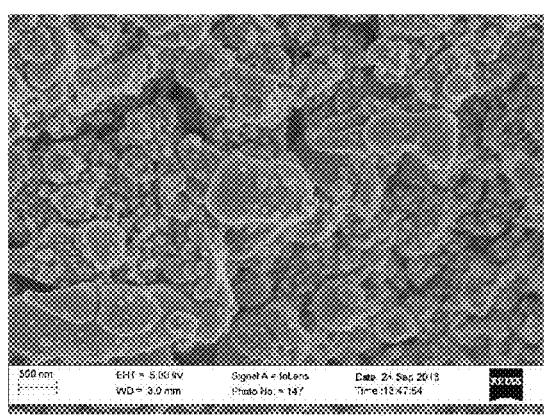

In this example, spot size was 50 μm and the offset step was 35 μm×50 μm. The scanning electron micrograms (SEMs) of FIG. 6 show the resulting structure. Image (a) shows a macro image of the substrate. Images (b)-(c) show the micro hillock structure forms ridges due to offset. The hillock structure is very shallow. Image (d) shows a periodic structure on the micro hillock walls. Image (e) shows nanoglobules with sphericity and with few voids. The polarization was 490 mV.

Trial D

Comparative

Figure 7:
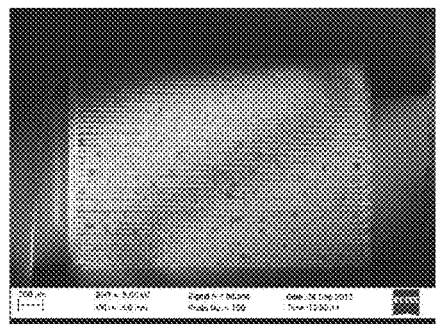
FIG. 7 shows an SEM of the substrate structure obtained according to Example 2, Trial D.
Figure 7:
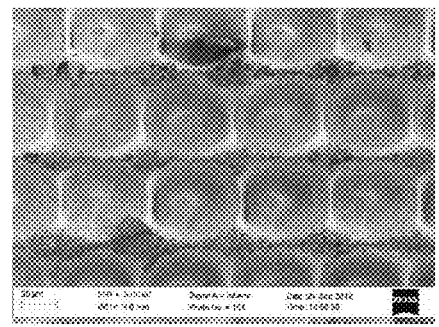
Figure 7:
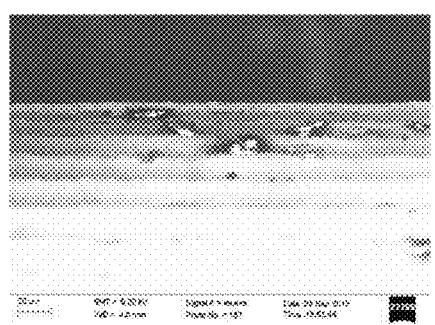
Figure 7:
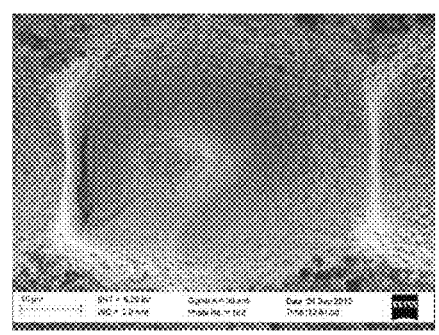
Figure 7:
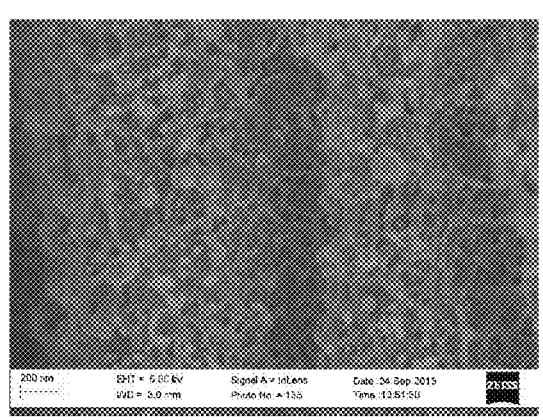

In this example, spot size was 50 μm and the offset step was 50 μm×50 μm. The scanning electron micrograms (SEMs) of FIG. 7 show the resulting structure. Image (a) shows a macro image of the substrate. Images (b)-(c) show the micro hillock structure forms ridges due to offset. The hillock structure is very shallow. Image (d) shows a periodic structure on the micro hillock walls. Image (e) shows nanoglobules with a mixture and tubular structure. The polarization was 710 mV.

Trial E

Figure 8:
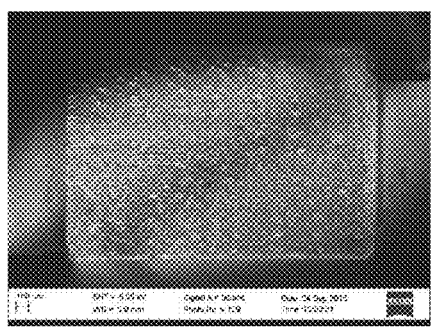
FIG. 8 shows an SEM of the substrate structure obtained according to Example 2, Trial E.
Figure 8:
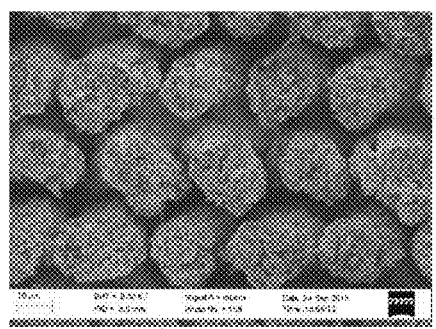
Figure 8:
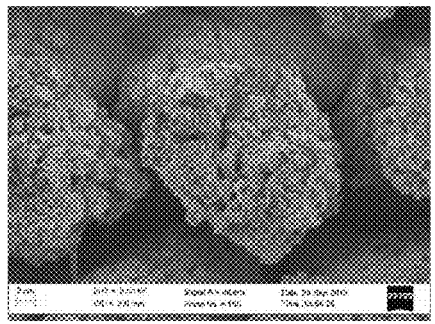
Figure 8:
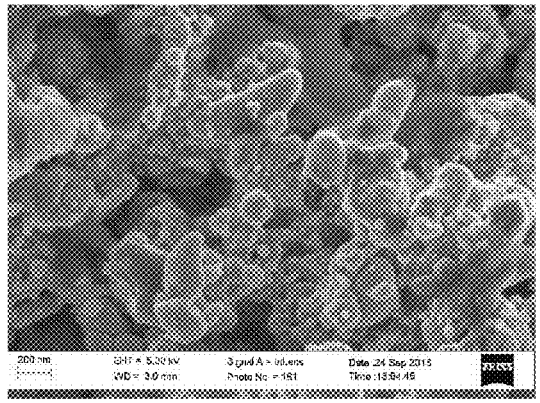

In this example, spot size was 50 μm and the offset step was 250 μm×25 μm. The scanning electron micrograms (SEMs) of FIG. 8 show the resulting structure. Image (a) shows a macro image of the substrate. Images (b)-(c) show the micro hillock structure forms ridges due to offset. The structure shows deep hillock features and some periodic structures can be seen on the hillock walls. Image (d) shows nanoglobules having sphericity and deep voids. The polarization was 185 mV.

Trial F

Figure 9:
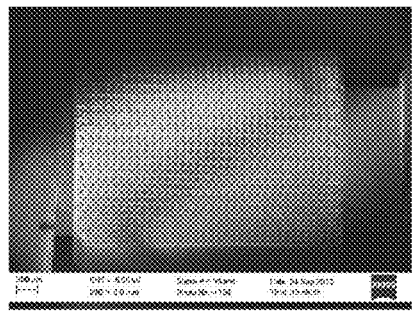
FIG. 9 shows an SEM of the substrate structure obtained according to Example 2, Trial F.
Figure 9:
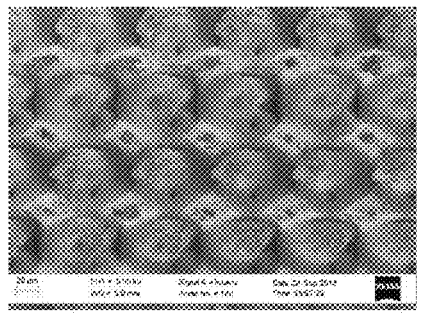
Figure 9:
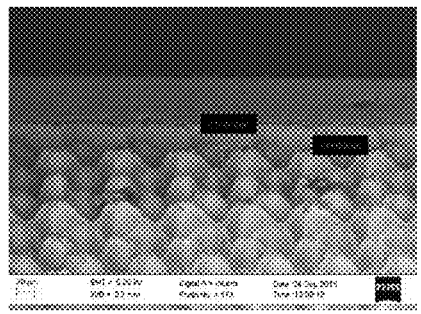
Figure 9:
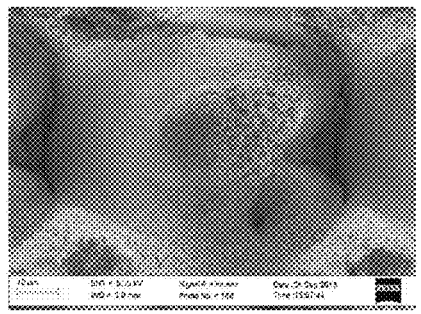
Figure 9:
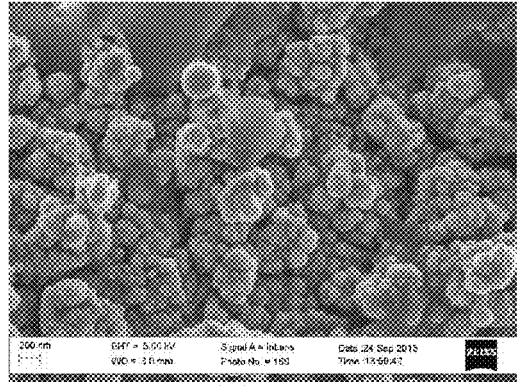

In this example, spot size was 100 μm and the offset step was 70 μm×70 μm. The scanning electron micrograms (SEMs) of FIG. 9 show the resulting structure. Image (a) shows a macro image of the substrate. Images (b)-(c) show the hillock structure offset and hillock features proportional to offset. Image (d) shows a periodic structure on the micro hillock walls. Image (e) shows nanoglobules with a sphericity and few voids. The polarization was 525 mV.

Trial G

Comparative

Figure 10:
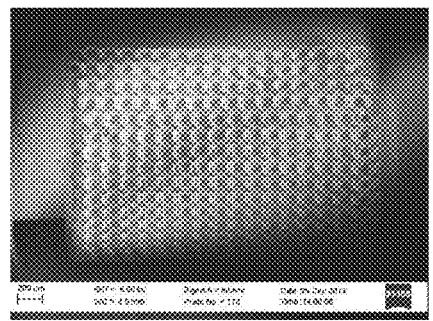
FIG. 10 shows an SEM of the substrate structure obtained according to Example 2, Trial G.
Figure 10:
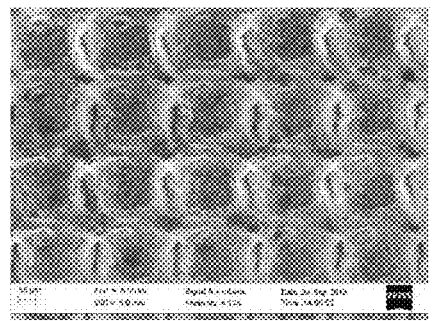
Figure 10:
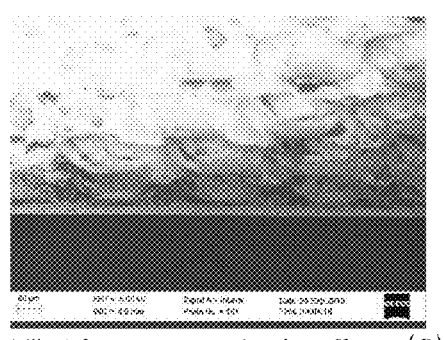
Figure 10:
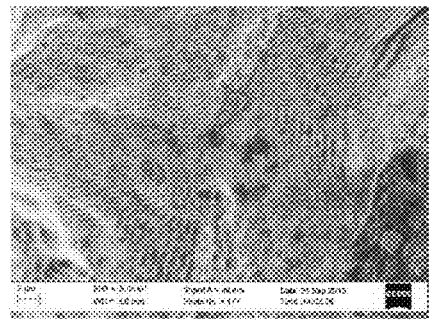
Figure 10:
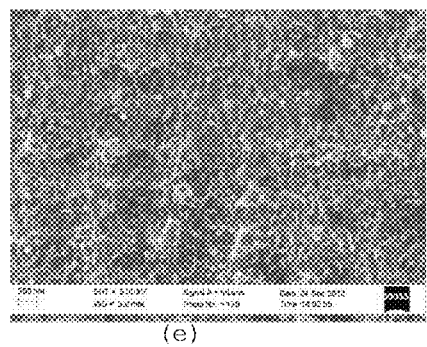

In this example, spot size was 200 μm and the offset step was 140 μm×140 μm. The scanning electron micrograms (SEMs) of FIG. 10 show the resulting structure. Image (a) shows a macro image of the substrate. Images (b)-(c) show the hillock structure offset and hillock features proportional to offset. Image (d) shows a periodic structure on the micro hillock walls. Image (e) shows nanoglobules with a tubular structures and few voids. The polarization was 630 mV.

These trials indicate that an important contribution to the performance of the structure was the overlap of the spots creating the hillock structure. The void width of the hillock structure is influenced by the laser spot size while the periodicity of the raised hillock structures is formed by the offset step. Similar patterns of nanoglobules such as in Trial C and Trial E gave very different results based upon a change in the macro-structured hillocks. It is preferred to have a series of raised structures with nanoglobules superimposed on those structures as in Trial E, as compared to a row of connected hillocks as in the case of Trial A and C. It is also preferred to have uniformly created mesa structures as in Trial E as compared to oblong structures as seen in Trial B. It is also preferred to optimize the size of the structure as comparing feature widths of Trial A to Trials F and G, and feature heights comparing Trial 1, Trial 2 and Trial 3. For the data presented it appears that smaller widths and deeper void depths are preferred. The nanoglobules are preferred to be in the form of spheres or angular globules which are well connect to the surface as compared to tubular structures such as in comparing Trial D to Trial F. The best performance also appears to come from nanoglobules structure with a high volume of voids such as in comparing Trial A to Trial D. The creation of the nanoglobules with a high volume of voids is influenced by the number of energy pulses in each individual spot as seen in Trials 1, 2 and 3. This effect is seen when the offset step is changed since an offset less than the spot size creates more pulses in some areas than in others. The co-influence can be seen by comparing Trials A and E. The micro structural period patters have a secondary effect on performance as they act as a nucleation site for the nanoglobules. The preferred mesa hillocks appear to have less pronounced periodic structures although this is likely due to the overcreation and nucleation of the nanoglobules rather than a lack of periodic structure.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An electrode comprising a solid, monolithic substrate having an outer peripheral surface; the outer peripheral surface having a topography defined by a plurality of discrete macro protrusions distributed about and extending outwardly from the outer peripheral surface, the macro protrusions having a width in the range of from about 0.15 µm to about 50 µm; a plurality of discrete micro protrusions distributed on and extending outwardly from the macro protrusions, the micro protrusions having a width ranging from about 0.15 µm to about 5 µm; and a plurality of discrete nano protrusions distributed on and extending outwardly from the micro protrusions, the nano protrusions having a width ranging from about 0.01 µm to about 1 µm.

2. The electrode of claim 1 wherein the macro protrusions are substantially uniformly distributed across the outer peripheral surface of the solid, monolithic substrate.

3. The electrode of claim 1 wherein the micro protrusions are distributed across the macro protrusions in the form of periodic waves of the heights of the micro protrusions.

4. The electrode of claim 1 wherein the nano protrusions are distributed across the micro protrusions in the form of tubes and/or globules.

5. The electrode of claim 1 wherein the macro protrusions have a width in the range of from about 0.2 µm to about 30 µm; the micro protrusions have a width in the range of from about 0.2 µm to about 2 µm; and the nano protrusions have a width in the range of from about 0.02 µm to about 1 µm.

6. The electrode of claim 1 wherein the macro protrusions have a width in the range of from about 1 µm to about 20 µm; the micro protrusions have a width in the range of from about 0.4 µm to about 1.5 µm; and the nano protrusions have a width in the range of from about 0.075 µm to about 0.8 µm.

7. The electrode of claim 1 wherein the substrate comprises a biocompatible metal.

8. The electrode of claim 1 wherein the substrate comprises platinum, steel, an alloy of platinum and iridium, an alloy of nickel and cobalt, titanium, an alloy of titanium, tantalum or combinations thereof.

9. The electrode of claim 1 wherein the outer peripheral surface further comprises a plurality of voids distributed about the outer peripheral surface and extending a depth through the substrate; said voids having a depth through the substrate of from about 50 nm to about 500 nm; and said voids having a width of from about 50 nm to about 500 nm; said voids being spaced from adjacent voids a distance of from about 50 nm to about 250 nm.

10. The electrode of claim 1 which has a configuration suitable for implanting within tissues of a mammal.

11. The electrode of claim 1 having an outer peripheral surface area of from about 1 $mm^2$ to about 20 $mm^2$.

12. The electrode of claim 1 further comprising at least one electrical connector electrically attached at an end thereof to the substrate.

13. The electrode of claim 12 further comprising an electrical pulse generator attached to another end of said electrical connector.

14. The electrode of claim 12 further comprising an electrical measurement device attached to another end of said electrical connector.

15. A method which comprises implanting the electrode of claim 1 within tissues of a mammal.

16. A method for producing an electrode comprising a solid, monolithic substrate having an outer peripheral surface; the outer peripheral surface having a topography defined by a plurality of discrete macro protrusions distributed about and extending outwardly from the outer peripheral surface, the macro protrusions having a width in the range of from about 0.15 µm to about 50 µm; a plurality of discrete micro protrusions distributed on and extending outwardly from the macro protrusions, the micro protrusions having a width ranging from about 0.15 µm to about 5 µm; and a plurality of discrete nano protrusions distributed on and extending outwardly from the micro protrusions, the nano protrusions having a width ranging from about 0.01 µm to about 1 µm; the method comprising exposing a solid, monolithic substrate to pulses of laser irradiation having a laser spot diameter ranging from about 1 µm to about 1000 µm, wherein the number of pulses of laser irradiation per spot, ranges from about 10 to about 1500 pulses, the pulse wavelength ranges from about 200 nm to about 1500 nm, the pulse width ranges from about 1 femtosecond to about 5 picoseconds; at a irradiance of from about 200 watts/$cm^2$ to about 5000 watts/$cm^2$.

17. The method of claim 16 wherein the exposing is conducted by traversing the spot of laser radiation across the outer peripheral surface of the solid, monolithic substrate at a rate of from about 50 mm/min to about 1000 mm/min.

18. The method of claim 16 wherein the substrate comprises a biocompatible metal.

19. The method of claim 16 wherein the laser has a spot diameter ranging from about 2 µm to about 250 µm; the number of pulses of laser irradiation per spot ranges from about 20 to about 1000; the laser has a pulse wavelength which ranges from about 400 to about 1,000; and the laser pulse width ranges from about 1 femtoseconds to about 3 picoseconds.

20. The method of claim 16 wherein the laser has a spot diameter ranging from about 5 µm to about 200 µm; the number of pulses of laser irradiation per spot ranges from about 100 to about 500; the laser has a pulse wavelength which ranges from about 400 to about 800; the laser pulse width ranges from about 1 femtoseconds to about 3 picoseconds.

* * * * *